US012569427B2

(12) United States Patent
Iida et al.

(10) Patent No.: US 12,569,427 B2
(45) **Date of Patent: *Mar. 10, 2026**

(54) MAKEUP APPLICATION METHOD

(71) Applicant: KAO CORPORATION, Tokyo (JP)

(72) Inventors: Masayuki Iida, Odawara (JP); Motoaki Ito, Odawara (JP); Yoko Hanada, Odawara (JP); Yukihiro Miyazaki, Odawara (JP)

(73) Assignee: KAO CORPORATION, Tokyo (JP)

( * ) Notice: Subject to any disclaimer, the term of this patent is extended or adjusted under 35 U.S.C. 154(b) by 545 days.

This patent is subject to a terminal disclaimer.

(21) Appl. No.: 17/995,270

(22) PCT Filed: Mar. 22, 2021

(86) PCT No.: PCT/JP2021/011781

§ 371 (c)(1),
(2) Date: Sep. 30, 2022

(87) PCT Pub. No.: WO2021/200351

PCT Pub. Date: Oct. 7, 2021

(65) Prior Publication Data

US 2023/0172836 A1 Jun. 8, 2023

(30) Foreign Application Priority Data

Apr. 1, 2020 (JP) ................................ 2020-066245

(51) Int. Cl.
*A61K 8/89* (2006.01)
*A61K 8/31* (2006.01)
*A61K 8/34* (2006.01)
*A61Q 1/00* (2006.01)

(52) U.S. Cl.
CPC .................. *A61K 8/89* (2013.01); *A61K 8/31* (2013.01); *A61K 8/345* (2013.01); *A61Q 1/00* (2013.01); *A61K 2800/59* (2013.01)

(58) Field of Classification Search
None
See application file for complete search history.

(56) References Cited

U.S. PATENT DOCUMENTS

| | | | |
|---|---|---|---|
| 2007/0134192 | A1 | 6/2007 | Shimizu et al. |
| 2010/0190950 | A1 | 7/2010 | Tetsuka et al. |
| 2011/0028571 | A1 | 2/2011 | Hayakawa |
| 2011/0301247 | A1 | 12/2011 | Hayakawa et al. |
| 2013/0150458 | A1 | 6/2013 | Iyoku |
| 2015/0202141 | A1 | 7/2015 | Sakuta et al. |
| 2018/0133144 | A1 | 5/2018 | Konishi et al. |
| 2020/0138692 | A1 | 5/2020 | Bichon et al. |

FOREIGN PATENT DOCUMENTS

| | | | | |
|---|---|---|---|---|
| CN | 103145995 | A | 6/2013 | |
| CN | 107613951 | A | 1/2018 | |
| CN | 110234312 | A | 9/2019 | |
| CN | 110520099 | A | 11/2019 | |
| CN | 110730653 | A | 1/2020 | |
| EP | 3308767 | A1 * | 4/2018 | ............ A61K 8/027 |
| JP | 10-045536 | A | 2/1998 | |
| JP | 2001-278729 | A | 10/2001 | |
| JP | 2002-322043 | A | 11/2002 | |
| JP | 2006-62995 | A | 3/2006 | |
| JP | 2010-174099 | A | 8/2010 | |
| JP | 2011-026263 | A | 2/2011 | |
| JP | 2012-017317 | A | 1/2012 | |
| JP | 2020-15699 | A | 1/2020 | |
| KR | 10-2015-0044104 | A | 4/2015 | |

OTHER PUBLICATIONS

Kim et al., "Influence of polyol and oil concentration in cosmetic products on skin moisturization and skin surface roughness", STIC, Publication date: Mar. 17, 2007. (Year: 2007).*

* cited by examiner

*Primary Examiner* — Kyung S Chang
(74) *Attorney, Agent, or Firm* — Oblon, McClelland, Maier & Neustadt, L.L.P.

(57) ABSTRACT

A method for makeup including (A) applying to skin a composition X including components (A1) and (A2). (A1) includes a polymer containing a norbornane moiety and/or a silicone-modified Pullulan and (A2) includes a volatile oil. The method further includes (B) applying to the skin a composition Y including a component (B1), other than the composition X, where (B1) includes one or more selected from the group consisting of polyols and liquid oils.

6 Claims, No Drawings

MAKEUP APPLICATION METHOD

CROSS REFERENCE TO RELATED APPLICATIONS

This application is a National Stage entry under 35 U.S.C. § 371 of PCT/JP2021/011781, filed on Mar. 22, 2021, and claims priority to Japanese Patent Application No. 2020-066245, filed on Apr. 1, 2020. The entire contents of both are incorporated herein by reference.

FIELD OF THE INVENTION

The present invention relates to a method for makeup.

BACKGROUND OF THE INVENTION

Conventionally, cosmetics compounded with a film-forming polymer are known which are intended to improve the uniformity of a makeup film and to extend makeup lasting. For example, Patent Literature 1 describes that a cosmetic containing a film-forming polymer in which a predetermined functional group is introduced into the skeleton of a polycycloolefin polymer allows makeup to last and achieves a favorable feel.

(Patent Literature 1): JP-A-2012-17317

SUMMARY OF THE INVENTION

The present invention relates to a method for makeup comprising:

(A) applying to a skin a composition X comprising components (A1) and (A2):
  (A1) a polymer comprising a norbornane moiety and/or a silicone-modified Pullulan; and
  (A2) a volatile oil; and
(B) applying to the skin a composition Y comprising a component (B1), other than the composition X:
  (B1) one or more selected from the group consisting of polyols and liquid oils.

The present invention also relates to a cosmetic kit for use in applying to a skin, comprising:

(A) a composition X comprising components (A1) and (A2):
  (A1) a polymer comprising a norbornane moiety and/or a silicone-modified Pullulan; and
  (A2) a volatile oil; and
(B) a composition Y comprising a component (B1), other than the composition X:
  (B1) one or more selected from the group consisting of polyols and liquid oils.

DETAILED DESCRIPTION OF THE INVENTION

Conventional cosmetics containing a film-forming polymer have had such problems that an uncomfortable feeling is caused immediately after application and a film formed thereby does not look nice.

The present inventors found that no uncomfortable feeling specific to polymers is caused immediately after application, the film has high adhesiveness, and coverage can be achieved with the film appearing transparent in a natural state by applying a composition Y comprising one or more selected from the group consisting of polyols and liquid oils before or after application of a composition X comprising a specific film-forming polymer and a volatile oil, and accomplished the present invention.

According to the present invention, no uncomfortable feeling specific to polymers is caused immediately after application, the film has high adhesiveness, and coverage can be achieved with the film appearing transparent in a natural state.

The present invention also has excellent effects of stretching skin wrinkles to make them less noticeable and of lifting the skin up to pull sagging of the skin up.

The term "skin wrinkles" means roughness or folds that occur on the skin surface, which are changes in the shape that occur because of sagging of the skin. Skin wrinkles are likely to occur around the mouth and the eyes, on the forehead, the neck, and the body, and the like. Small folds are fine wrinkles, and large folds are large wrinkles, which occur with a flow of enlarged skin pores of nasolabial folds, cheek folds, and the like.

<Component (A1)>

In the present invention, the component (A1) used in the composition X is (A11) a polymer comprising a norbornane moiety and/or (A12) a silicone-modified Pullulan.

When the composition comprising the component (A1) is applied to the skin by coating or the like and then dried, shrinkage occurs in the film containing the component (A1) as well as in the skin surface attached to the film. The component (A1) is also excellent in bend resistance, and thus a film containing the component (A1) is unlikely to crack and likely to shrink while following the skin shape. Accordingly, also when the film containing the component (A1) shrinks, sufficient adhesiveness between the film and the skin surface can be obtained.

Among the component (A1), in (A11) the polymer comprising a norbornane moiety, the norbornane moiety means a structure of the following formula. It is sufficient that the polymer (A11) has the structure of the following formula at an arbitrary site in the polymer (A11).

The component (A11) is not particularly limited as long as the component (A11) is a polymer having the norbornane moiety described above in the molecule, but the component (A11) is even more preferably a silicone-modified polymer containing a norbornane moiety, in view of increasing shrinkage and adhesiveness to the skin of the coating film by means of the mechanism of action mentioned above.

Examples of the silicone-modified polymer containing a norbornane moiety include polymers having a repeating unit of the following formula (1) or (2):

(1)

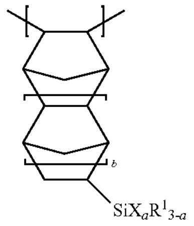

wherein $R^1$ is each independently an alkyl group having one or more and 12 or less carbon atoms, X is a group of the following formula (i). a is an integer of 1 or above and 3 or below, and b is an integer of 0 or above and 2 or below.

(i)

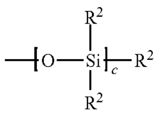

wherein $R^2$ is each independently a hydrocarbon group having one or more and 12 or less carbon atoms, and c is an integer of 1 or above and 5 or below.

(2)

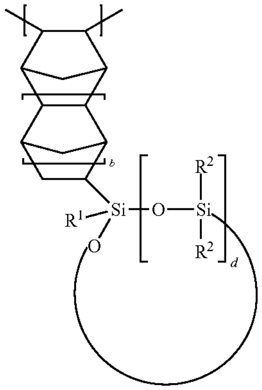

wherein $R^1$, $R^2$, and b are the same as described above, and d is an integer of 2 or above and 5 or below.

In the formula (1), $R^1$ is each independently an alkyl group having one or more and 12 or less carbon atoms, and in view of the skin wrinkle-reducing effect and versatility, $R^1$ is preferably methyl group, ethyl group, n-propyl group, butyl group, or pentyl group, more preferably methyl group.

X is a group of the formula (i). In the formula (i), $R^2$ is each independently a hydrocarbon group having one or more and 12 or less carbon atoms. In view of the skin wrinkle-reducing effect and in view of versatility, $R^2$ is preferably an alkyl group having one or more and 12 or less carbon atoms or an aryl group having six or more and 12 or less carbon atoms, more preferably an alkyl group or a phenyl group having one or more and 12 or less carbon atoms, even more preferably an alkyl group having one or more and three or less carbon atoms, even more preferably methyl group. c is an integer of 1 or above and 5 or below, and in view of versatility, c is preferably equal to 1. Specifically, X is preferably a trimethylsiloxy group.

a is an integer of 1 or above and 3 or below, and the polymer may be, for example, a polymer having a mixture of a repeating unit with a being 2 and a repeating unit with a being 3. In view of versatility, a is preferably 3. b is an integer of 0 or above and 2 or below, and in the same view, b is preferably 0, 1, or a combination thereof, more preferably 0.

In the formula (2), $R^1$, $R^2$, and b are the same as described above. d is an integer of 2 or above and 5 or below, and in view of versatility, d is preferably equal to 2. In the cyclic silicone structure in the formula (2), it is preferred in the same view that $R^1$ and $R^2$ are methyl group, and that d is 2 or 3. Specifically, the cyclic silicone structure in the formula (2) is preferably a structure of the following formula (4) or (5):

(4)

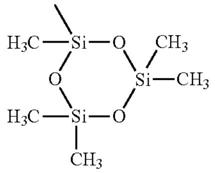

(5)

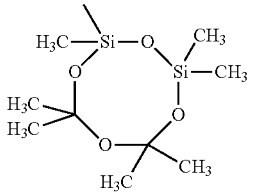

In view of the skin wrinkle-reducing effect, the proportion of repeating units of the formula (1) or (2) in a silicone-modified polymer containing a norbornane moiety is preferably 10% or higher, more preferably 30% or higher, even more preferably 50% or higher of the number of all repeating units in the polymer. The upper limit is 100%, and the proportion is preferably 95% or lower, more preferably 90% or lower, even more preferably 70% or lower. In a silicone-modified polymer containing a norbornane moiety, the specific range of the number of repeating units of the formula (1) or (2) is preferably from 10% to 100%, more preferably from 10% to 95%, even more preferably from 30% to 90%, even more preferably from 50% to 70% of the number of all repeating units in the polymer.

A silicone-modified polymer containing a norbornane moiety may have a repeating unit of the following formula (3) in addition to the repeating unit of the formula (1) or (2).

(3)

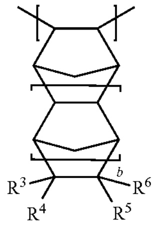

wherein $R^3$ to $R^6$ are each independently a substituent group selected from the group consisting of a hydrogen atom; a halogen atom; an alkyl group, an alkenyl group, a cycloalkyl group, an aryl group, an alkoxy group, an aryloxy group, and a halogenated hydrocarbon group which have one or more and 10 or less carbon atoms; an oxetanyl group, an alkoxycarbonyl group, a polyoxyalkylene group, a polyglyceryl group, and an alkoxysilyl group. Two groups chosen from $R^3$ to $R^6$ may be taken together to form an aliphatic ring structure, an aromatic ring structure, a carboimide group, or an acid anhydride group. b is the same as described above.

In view of the skin wrinkle-reducing effect, the proportion of the above-described repeating units of the formula (3) in a silicone-modified polymer containing a norbornane moiety is preferably 90% or lower, more preferably 70% or lower, even more preferably 50% or lower of the number of all repeating units in the polymer. Further, when the above-described repeating units of the formula (3) are contained, the proportion thereof is preferably 5% or higher, more preferably 10% or higher, even more preferably 30% or higher of the number of all repeating units in the polymer. In a silicone-modified polymer containing a norbornane moiety, the specific range of the number of repeating units of the formula (3) is preferably from 5% to 90%, more preferably from 10% to 70%, even more preferably from 30% to 50% of the number of all repeating units in the polymer.

The proportion of the above-described repeating units of the formulas (1) to (3) in the silicone-modified polymer containing a norbornane moiety can be obtained by $^1$H-NMR measurement.

The silicone-modified polymer containing a norbornane moiety is preferably a silicone-modified polynorbornene, more preferably a silicone-modified polynorbornene of the following formula (6):

(6)

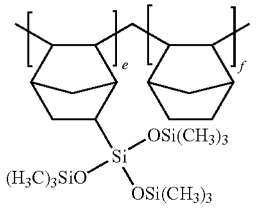

wherein e and f are the number of repeating units and are each independently an integer of 1 or above.

In view of the skin wrinkle-reducing effect, the ratio of e and f, e/f, in the formula (6) is preferably from 20/80 to 90/10 (mol/mol), more preferably from 30/70 to 80/20 (mol/mol), even more preferably from 50/50 to 70/30 (mol/mol).

In view of balancing shrinkage and bend resistance and in view of the skin wrinkle-reducing effect, the number average molecular weight (Mn) of a silicone-modified polymer containing a norbornane moiety is preferably 50,000 or more, more preferably 100,000 or more, even more preferably 200,000 or more, and preferably 2,000,000 or less, more preferably 1,500,000 or less, even more preferably 800,000 or less, even more preferably 600,000 or less. The specific range of the number average molecular weight (Mn) of a silicone-modified polymer containing a norbornane moiety is preferably from 50,000 to 2,000,000, more preferably from 100,000 to 1,500,000, even more preferably from 200,000 to 800,000, even more preferably from 200,000 to 600,000.

The number average molecular weight (Mn) of the polymer can be measured by gel filtration chromatography (GPC) using polystyrene as a reference substance, and specifically by the methods described in the examples.

The component (A11) can be obtained by, for example, a known method of addition polymerization of a cyclic olefin monomer which contains a norbornane moiety or can form a norbornane moiety.

For example, when the component (A11) is the above-described silicone-modified polymer containing a norbornane moiety having the repeating unit of the formula (1) or (2), it can be obtained by addition polymerization of a cyclic olefin monomer of the following formula (1a) or (2a). Further, a cyclic olefin monomer of the formula (3a) may be copolymerized.

(1a)

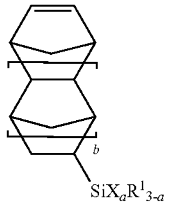

wherein $R^1$ is each independently an alkyl group having one or more and 12 or less carbon atoms, and X is a group of the following formula (i). a is an integer of 1 or above and 3 or below, and b is an integer of 0 or above and 2 or below.

(i)

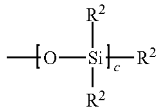

wherein $R^2$ is each independently a hydrocarbon group having one or more and 12 or less carbon atoms, and c is an integer of 1 or above and 5 or below.

(2a)

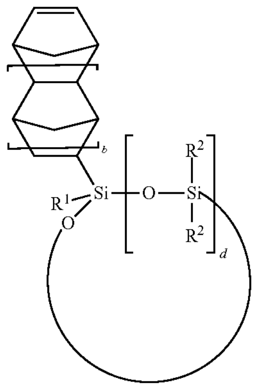

wherein $R^1$, $R^2$, and b are the same as described above, and d is an integer of 2 or above and 5 or below.

(3a)

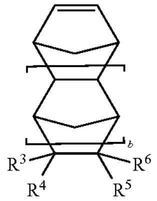

wherein $R^3$ to $R^6$ are each independently a substituent group selected from the group consisting of a hydrogen atom; a halogen atom; an alkyl group, an alkenyl group, a cycloalkyl group, an aryl group, an alkoxy group, an aryloxy group, and a halogenated hydrocarbon group which have one or more and 10 or less carbon atoms; an oxetanyl group; an alkoxycarbonyl group; a polyoxyalkylene group; a polyglyceryl group; and an alkoxysilyl group. Two groups chosen from $R^3$ to $R^6$ may be taken together to form an aliphatic ring structure, an aromatic ring structure, a carboimide group, or an acid anhydride group. b is the same as described above.

When the above-described cyclic olefin monomer of the formula (3a) is copolymerized, the use amount thereof is, in view of the skin wrinkle-reducing effect, preferably 90 mol % or less, more preferably 70 mol % or less, even more preferably 50 mol % or less, and preferably 5 mol % or more, more preferably 10 mol % or more, even more preferably 30 mol % or more, assuming the amount of all monomers used for polymerization as 100 mol %.

The above-described silicone-modified polynorbornene of the formula (6) can be obtained by addition polymerization of tris(trimethylsiloxy)silylnorbornene of the following formula (6a) and norbornene:

(6a)

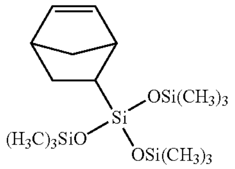

In view of increasing shrinkage and adhesiveness to the skin of the coating film, the copolymerization ratio of tris(trimethylsiloxy)silylnorbornene and norbornene is preferably from 20/80 to 90/10 (mol/mol), more preferably from 30/70 to 80/20 (mol/mol), even more preferably from 50/50 to 70/30 (mol/mol).

Of note, all the repeating units of the formulas (1) to (3) and (6) represent a unit of a 2,3-addition structure of a cyclic olefin monomer as a raw material monomer and may contain a unit of a 2,7-addition structure obtained by addition polymerization of the cyclic olefin monomer.

The silicone-modified polymer containing a norbornane moiety is preferably a (norbornene/tris(trimethylsiloxy)silylnorbornene) copolymer, i.e., a compound which is expressed as NORBORNENE/TRIS(TRIMETHYLSILOXY)SILYLNORBORNENE COPOLYMER, as the INCI name (International Cosmetic Ingredient Dictionary and Handbook, 16th Edition, Volume 2, 2016, p. 2274).

Examples of the commercially available silicone-modified polymer containing a norbornane moiety include "NBN-30-ID" (an isododecane solution of a norbornene/tris(trimethylsiloxy)silylnorbornene) copolymer) manufactured by Shin-Etsu Chemical Co., Ltd.

Among the component (A1), examples of the (A12) silicone-modified *Pullulans* include *Pullulans* having a silicone structure in a side chain. Specifically, in view of increasing shrinkage and adhesiveness to the skin of the coating film, a silicone-modified Pullulan in which at least some hydrogen atoms of an OH group in the Pullulan is substituted with a group of the following formula (7) is preferred:

$$-Z^1-SiX_aR^1_{3-a} \quad (7)$$

wherein $Z^1$ is a single bond or divalent organic group. $R^1$, X, and a are the same as described above, and in the same view, X is preferably trimethylsiloxy group, and a is preferably 3.

In the same view, in the formula (7), $Z^1$ is preferably a divalent organic group, more preferably a divalent group of the following formula (8) or (9), even more preferably a divalent group of the following formula (8)

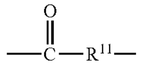

(9)

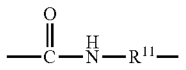

wherein $R^{11}$ is an alkylene group having one or more and 10 or less carbon atoms, and examples thereof include methylene group, ethylene group, trimethylene group, propylene group, and butylene group. Of these, in the same view, ethylene group, trimethylene group, and propylene group are preferred, and trimethylene group and propylene group are more preferred.

Examples of the commercially available silicone-modified *Pullulans* include "TSPL-30-ID" (an isododecane solution of tri(trimethylsiloxy)silyl propyl carbamide acid Pullulan) and "TSPL-30-D5" (a cyclopentasiloxane solution of tri(trimethylsiloxy)silyl propyl carbamide acid *Pullulan*), which are manufactured by Shin-Etsu Chemical Co., Ltd.

In view of increasing shrinkage and adhesiveness to the skin of the coating film, the component (A1) is preferably (A11) the polymer containing a norbornane moiety, more preferably a silicone-modified polymer containing a norbornane moiety.

As the component (A1), one or more of polymers containing a norbornane moiety and silicone-modified *Pullulans* can be used in combination. In view of increasing shrinkage and adhesiveness to the skin of the coating film, the content of the solid content is preferably 0.01 mass % or more, more preferably 1 mass % or more, even more preferably 2 mass % or more, even more preferably 4 mass % or more, even more preferably 5 mass % or more, and preferably 30 mass % or less, more preferably 28 mass % or less, even more preferably 25 mass % or less, even more preferably 20 mass % or less, even more preferably 18 mass % or less in the composition X. Further, the content of the solid content of the component (A1) is preferably from 0.01 to 30 mass %, more preferably from 1 to 28 mass %, even more preferably from 2 to 25 mass %, even more preferably from 4 to 20 mass %, even more preferably from 5 to 18 mass % in the composition X.

<Component (A2)>

The component (A2) used in the present invention is a volatile oil. Volatility refers to having a flash point of 35° C. or higher and less than 90° C.

As the volatile oil of the component (A2), one or more selected from the group consisting of volatile silicone oils and volatile hydrocarbon oils are preferable.

Examples of the volatile silicone oils include straight polydimethylsiloxanes such as hexamethyldisiloxane, octamethyltrisiloxane, polydimethylsiloxane (1cs), polydimethylsiloxane (1.5cs), and polydimethylsiloxane (2cs); branched siloxanes such as methyl trimethicone, tris(trimethylsilyl)methylsilane, and tetrakis(trimethylsilyl)silane; and cyclic dimethylsiloxanes such as octamethylcyclotetrasiloxane, decamethylcyclopentasiloxane, and dodecamethylcyclohexasiloxane.

Examples of the volatile hydrocarbon oils include paraffinic hydrocarbon oils such as n-decane, n-undecane, and n-dodecane; isoparaffinic hydrocarbon oils such as isodecane, isododecane, and hydrogenated polyisobutene; and cyclic paraffin hydrocarbon oils such as cyclodecane and cyclododecane. Of these, hydrocarbon oils having from 8 to 16 carbon atoms are preferred, hydrocarbon oils having from 10 to 16 carbon atoms are more preferred, and hydrocarbon oils having 12 carbon atoms are even more preferred.

As the volatile oil of the component (A2), one or more selected from the group consisting of isodecane, hexamethyldisiloxane, methyl trimethicone, and polydimethylsiloxane having kinematic viscosity of 2 cSt or lower at 25° C. are preferred, and one or more selected from the group consisting of isododecane, hexamethyldisiloxane, methyl trimethicone, and octamethylpolydimethylsiloxane are more preferred. Of note, the kinematic viscosity can be measured by, for example, using an Ubbelohde's viscometer.

In view of increasing shrinkage and adhesiveness to the skin of the coating film, the component (A2) is more preferably one or more selected from the group consisting of isododecane, hexamethyldisiloxane, and polydimethylsiloxane having kinematic viscosity of 1.5 cSt or lower at 25° C., even more preferably one or more selected from the group consisting of hexamethyldisiloxane and polydimethylsiloxane having kinematic viscosity of 1 cSt or lower at 25° C., even more preferably hexamethyldisiloxane.

Examples of the commercially available hexamethyldisiloxane and polydimethylsiloxane having kinematic viscosity of 2 cSt or lower at 25° C. include "KF-96L-0.65cs" (hexamethyldisiloxane), "TMF1.5," "KF-96L-1cs" (octamethyltrisiloxane), "KF-96L-1.5cs," and "KF-96L-2cs," which are manufactured by Shin-Etsu Chemical Co., Ltd., "SH200C Fluid 1cs" and "SH200C Fluid 1.5cs," which are manufactured by Dow Corning Toray Co., Ltd., "TSF451-0.65" manufactured by Momentive Performance Materials Japan LLC, and "BELSIL DM0.65" manufactured by Wacker Asahikasei Silicone Co., Ltd.

As the component (A2), one or more can be used in combination. In view of increasing shrinkage and adhesiveness to the skin of the coating film, the content thereof is preferably 1 mass % or more, more preferably 30 mass % or more, even more preferably 50 mass % or more, even more preferably 70 mass % or more, and preferably 98 mass % or less, more preferably 97 mass % or less, even more preferably 94 mass % or less, even more preferably 93 mass % or less in the composition X. Further, the content of the component (A2) is preferably from 1 to 98 mass %, more preferably from 30 to 97 mass %, even more preferably from 50 to 94 mass %, even more preferably from 70 to 93 mass % in the composition X.

In the composition X, in view of increasing shrinkage and adhesiveness to the skin of the coating film, a mass ratio of the component (A1) to the component (A2), (A1)/(A2), is preferably 0.002 or higher, more preferably 0.02 or higher, even more preferably 0.04 or higher, even more preferably 0.05 or higher, and preferably 1 or lower, more preferably 0.7 or lower, even more preferably 0.4 or lower, even more preferably 0.2 or lower. Further, a mass ratio of the component (A1) to the component (A2), (A1)/(A2), is preferably from 0.002 to 1, more preferably from 0.02 to 0.7, even more preferably from 0.04 to 0.4, even more preferably from 0.05 to 0.2.

<Component (A3)>

In the present invention, the composition X can further comprise (A3) a powder, which serves to increase shrinkage and adhesiveness to the skin of the coating film, and when used in combination with the composition Y, can prevent an uncomfortable feeling.

Such a powder may be any of organic powders, inorganic powders, and the like.

Examples of the organic powders include polyamide resins, nylon resins, polyester resins, polyethylene resins, polytetrafluoroethylene resins, polypropylene resins, polystyrene resins, benzoguanamine resins, polymethyl benzoguanamine resins, polymethyl methacrylate, polyurethane resins, vinyl resins, fluorine resins, acrylic resins, and melamine resins; silicone resins such as silicone elastomer obtained by crosslinking dimethylsilicone and polymethylsilsesquioxane; and crosslinked or uncrosslinked organic powders such as powders of one or more polymers or copolymers selected from the group consisting of poly (meth)acrylic acid, sodium poly(meth)acrylate, poly(meth) acrylic acid esters, and alkylene glycol poly(meth)acrylate such as butyl acrylate-vinyl acetate copolymers, styrene-acrylic acid copolymers, divinylbenzene-styrene copolymers, and (lauryl methacrylate/ethylene glycol dimethacrylate)copolymers.

Examples of the inorganic powders include talc, kaolin, mica, sericite, phlogopite, magnesium aluminum silicate, calcium silicate, aluminum silicate, magnesium silicate, barium silicate, strontium silicate, epoxy-treated aluminum, aluminum powder, calcium phosphate, silicic anhydride, anhydrous aluminum silicate, pyrophyllite clay, bentonite, smectite, montmorillonite, vermiculite, hectorite, zeolite, higilite, silica, alumina, zirconia, iron oxides (red iron oxide, yellow iron oxide, black iron oxide, and γ-iron oxide), yellow ochre, black titanium oxide, low-valent titanium oxide, iron titanate, zinc oxide, aluminum hydroxide, aluminum oxide, cobalt aluminum oxide, chromium oxide, zirconium oxide, titanium oxide, titanium oxide sol, iron oxide-titanium dioxide sinter, cerium oxide, magnesium oxide, chromium hydroxide, titanium-titanium dioxide sinter, cobalt titanate, manganese violet, cobalt violet, calcium carbonate, barium carbonate, magnesium carbonate, tungstate metal salts, barium sulfate, calcined calcium sulfate (calcined gypsum), bismuth oxychloride, calamine, sodium rosinate-treated magnesium oxide, fluorine apatite, hydroxyapatite, ceramic powder, and metal soap (such as zinc myristate, calcium palmitate, and aluminum stearate) and also include composite powders of two or more of these. Examples thereof further include organic-inorganic composite powders such as acrylic resin-coated aluminum powder, titanium oxide-coated nylon powder.

Examples of the powders of natural fiber include silk powder, wool powder, and cellulose powder.

Examples of the pearlescent pigments include titanated mica, iron oxide-coated titanated mica, titanium oxide-coated bismuth oxychloride, titanium oxide-coated talc, titanium oxide-coated glass flakes, and fish scale flakes.

These powders may be used as they are, or may be hydrophobized before use.

Such hydrophobization is not limited as long as it is a treatment applied to usual powders for cosmetics, and example thereof include a silicone treatment, an alkoxysilane treatment, a fatty acid treatment, a lauroyl lysine treatment, a lecitin treatment, a N-acyl amino acid treatment, a metal soap treatment, and a fluorine compound treatment. Of these, a silicone treatment is preferred. These treatments may be conducted by usual methods.

As the component (A3), one or more can be used in combination. In view of increasing shrinkage and adhesiveness to the skin of the coating film and preventing an uncomfortable feeling by use in combination with the composition Y, the content thereof is preferably 0.1 mass % or more, more preferably 1 mass % or more, even more preferably 2 mass % or more, even more preferably 3 mass % or more, and preferably 40 mass % or less, more preferably 20 mass % or less, even more preferably 15 mass % or less, even more preferably 10 mass % or less in the composition X. Further, the content of the component (A3) is preferably from 0.1 to 40 mass %, more preferably from 1 to 20 mass %, even more preferably from 2 to 15 mass %, even more preferably from 3 to 10 mass % in the composition X.

<Component (A4)>

In the present invention, the composition X can further contain (A4) a surfactant, and preferred examples thereof include anionic surfactants, cationic surfactants, nonionic surfactants, and ampholytic surfactants.

Surfactants as the component (A4) are not limited as long as they are used for usual agents for skin external use, but they are preferably nonionic surfactants in view of being soluble in a volatile oil and preventing stickiness.

Examples of the nonionic surfactants include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene fatty acid ester, polyoxyethylene sorbitan fatty acid ester, polyoxyethylenealkyl ether, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene hydrogenated castor oils and fatty acid ester, polyoxyethylene phytostanol ether, polyoxyethylene phytosterose ether, polyoxyethylene cholestanol ether, polyoxyethylene cholesteryl ether, alkyl glyceryl ether-modified silicone, polyoxyalkylene-modified silicone, polyoxyalkylene-alkyl co-modified silicone, and polyoxyalkylene-fluoroalkyl co-modified silicone.

Of these, in view of increasing dispersibility/solubility of water and water-soluble components in an oil, a nonionic surfactant is preferably a silicone surfactant, and even more preferably comprises one or more alkyl glyceryl ether-modified silicones and polyoxyalkylene-modified silicones, even more preferably polyoxyalkylene-modified silicones.

Examples of the polyoxyalkylene-modified silicones which can be used include commercially available products such as SH3771M, SH3772M, SH3773M, SH3775M, SH3749, and DC5200, which are manufactured by Dow Corning Toray Co., Ltd, and KF-6011, KF-6012, KF-6013, KF-6015, KF-6016, KF6017, and KF-6004, which are manufactured by Shin-Etsu Chemical Co., Ltd.

In view of increasing dispersibility/solubility of water and water-soluble components in an oil, the HLB value of a nonionic surfactant is preferably 1 or higher and 7 or lower, more preferably 2 or higher and 6 or lower.

Here, HLB (Hydrophilic-Lipophilic Balance) represents the proportion of the molecular weight of a hydrophilic portion to the molecular weight of the whole surfactant and can be obtained by the Griffin's formula for nonionic surfactants.

The HLB value of a mixed surfactant composed of two or more nonionic surfactants is obtained as follows. The HLB of the mixed surfactant is obtained by calculating an arithmetic mean of the HLB values of each nonionic surfactant based on the mixing ratio.

$$\text{Mixed HLB}=\Sigma(\text{HLBx}\times\text{Wx})/\Sigma\text{Wx}$$

HLBx represents the HLB value of a nonionic surfactant X.

Wx represents weight (g) of the nonionic surfactant X having the HLBx value.

One or more different nonionic surfactants can be used in combination, and in view of being soluble in a volatile oil and preventing stickiness, the content of the nonionic surfactants is preferably 30 mass % or less, more preferably 10 mass % or less, even more preferably 5 mass % or less, even more preferably 3 mass % or less, even more preferably 1 mass % or less in the composition X.

<Other Components>

In the composition X, the content of water is preferably 50 mass % or less, more preferably 30 mass % or less, even more preferably 10 mass % or less, even more preferably 5 mass % or less, even more preferably 1 mass % or less in the composition X.

In addition to the above-described components, the composition X can optionally contain various components usually used as long as the effect of the present invention is not impaired. Examples of these components include oily components other than described above, water-soluble polymers, antioxidants, ultraviolet absorbers, vitamins, preservatives, pH modifiers, perfumes, plant extracts, moisturizers, colorants, cooling sensation agents, antiperspirants, sterilizers, and skin activators.

The composition X can be manufactured by usual methods using the components (A1) and (A2) and, if necessary, other components and can be applied to any forms such as aqueous compositions, oily compositions, and emulsified compositions. The composition X can be applied as a preparation such as a liquid, a milky lotion, a paste, a cream, a gel, a solid, or a sheet.

The composition may be any of those which can be used for cosmetics, quasi-drugs, and drugs and can be used as skin care cosmetics such as lotions, milky lotions, creams, beauty essences, dispersions, gels, ointments, facial masks, mousses, aerosols, poultices, and cleansing agents.

<Component (B1)>

In the present invention, the component (B1) used in the composition Y is one or more selected from the group consisting of (B11) a polyol and (B12) a liquid oil.

Among the component (B1), (B11) the polyol may be any of compounds which have 2 or more hydroxyl groups in the molecule and are used for usual agents for skin external use.

Examples of the dihydric alcohols include ethylene glycol, diethylene glycol, triethylene glycol, polyethylene glycol, propylene glycol, dipropylene glycol, tripropylene glycol, polypropylene glycol, butylene glycol, and propanediol. Examples of the trihydric alcohols include glycerin and trimethylolpropane. Examples of the tetrahydric alcohols include diglycerin and erythritol. Examples of the pentahydric or higher polyhydric alcohols include polyglycerins such as triglycerin; and sugars and sugar alcohols such as glucose, maltose, maltitose, sucrose, xylitol, sorbitol, mannitol, polyoxyethylene methyl glucoside, polyoxyethylene ethyl glucoside, and polyoxyethylene propylene glucoside.

In view of preventing an uncomfortable feeling specific to polymers immediately after application of the composition X, increasing the adhesiveness of the film, and achieving coverage with the film appearing transparent in a natural state, the component (B11) is preferably one or more selected from the group consisting of dihydric alcohols and trihydric alcohols, more preferably comprises one or more selected from the group consisting of polyethylene glycol, dipropylene glycol, butylene glycol, propanediol, and glycerin, even more preferably comprises at least glycerin.

Among the component (B1), (B12) the liquid oil has flowability at 25° C.

Such a liquid oil may be any liquid oil as long as it is used for usual cosmetics, and examples thereof include straight or branched hydrocarbon oils such as liquid paraffin, light liquid isoparaffin, heavy liquid isoparaffin, mineral oil, squalane, α-olefin oligomers, polyisobutylene, polybutene, hydrogenated polyisobutene, and hydrogenated polydecene; ester oils such as isononyl isononanoate, isodecyl isononanoate, isotridecyl isononanoate, tricyclodecane methyl isononanoate, ethyl isostearate, isobutyl isostearate, isopropyl isostearate, 2-hexyldecyl isostearate, di-2-ethylhexyl succinate, bis-ethoxydiglycol succinate, hexyl laurate, propanediol di(caprylate/caprate), neopentyl glycol diisononanoate, neopentyl glycol dicaprate, glyceryl monostearate monomyristate, glyceryl diisostearate, polyglyceryl diisostearate, propanediol diisostearate, trimethylolpropane triisostearate, glyceryl triisostearate, diglyceryl triisostearate, diglyceryl tetraisostearate, diisostearyl malate, octyldodecyl malate, glycerin fatty acid esters, octyldodecyl myristate, isopropyl myristate, 2-ethylhexyl palmitate, isopropyl palmitate, cetyl 2-ethylhexanoate, trimethylolpropane tri-2-ethylhexanoate, glyceryl tri-2-ethylhexanoate, octyldodecyl myristate, 2-hexyldecyl myristate, 2-hexyldecyl 2-ethylhexanoate, neopentyl glycol di-2-ethylhexanoate, 2-ethylhexyl hydroxystearate, glyceryl tri(caprylate/caprate), glyceryl trioctanoate, neopentyl glycol dioctanoate, octyl methoxycinnamate, 2-ethylhexyl p-methoxycinnamate, and propylene carbonate; ether oils such as cetyl dimethyl butyl ether, dicaprylyl ether; higher alcohols having a straight or branched alkyl or alkenyl group having from 10 to 24 carbon atoms such as lauryl alcohol, myristyl alcohol, isocetyl alcohol, isostearyl alcohol, 2-octyldodecanol, and oleyl alcohol; silicone oils such as dimethylpolysiloxane, dimethylcyclopolysiloxane, methylphenylpolysiloxane, methylhydrogenpolysiloxane, polyether-modified silicone, acryl-modified silicone, fluorine-modified silicone, and higher alcohol-modified organopolysiloxane; fluorine oils such as fluoropolyether, perfluoroalkylether silicone, and fluorine-modified silicone; and phenoxyethanol, and tocopherol.

In view of preventing an uncomfortable feeling specific to polymers immediately after application of the composition X, increasing the adhesiveness of the film, and achieving coverage with the film appearing transparent in a natural state, the component (B12) is preferably one or more selected from the group consisting of straight or branched hydrocarbon oils, ester oils, higher alcohols having a straight or branched alkyl or alkenyl group having from 10 to 24 carbon atoms, silicone oils, and phenoxyethanol, preferably one or more selected from the group consisting of straight or branched hydrocarbon oils, ester oils, silicone oils, and phenoxyethanol, more preferably one or more selected from the group consisting of liquid paraffin, squalane, hydrogenated polyisobutene, neopentyl glycol dicaprate, glyceryl monostearate monomyristate, polydimetylsiloxane, and phenoxyethanol.

As the component (B1), one or more can be used in combination. In view of preventing an uncomfortable feeling specific to polymers immediately after application of the composition X, increasing the adhesiveness of the film, and achieving coverage with the film appearing transparent in a natural state, the content thereof is preferably 1 mass % or more, more preferably 5 mass % or more, even more preferably 10 mass % or more, and preferably 95 mass % or less, more preferably 80 mass % or less, even more preferably 40 mass % or less in the composition Y. Further, the content of the component (B1) is preferably from 1 to 95 mass %, more preferably from 5 to 80 mass %, even more preferably from 10 to 40 mass % in the composition Y.

<Other Components>

In addition to the component (B1), the composition Y can optionally contains various components usually used as long as the effect of the present invention is not impaired. Examples of these components include oily components other than described above, powders, surfactants, water-soluble polymers, antioxidants, ultraviolet absorbers, vitamins, preservatives, pH modifiers, Perfumes, plant extracts, moisturizers, colorants, cooling sensation agents, antiperspirants, sterilizers, skin activators, and water.

The composition Y is a composition other than the composition X.

The composition Y can be manufactured by usual methods using the component (B1) and other components and can be applied to any forms such as aqueous compositions, oily compositions, and emulsified compositions. The composition can be applied as a preparation such as a liquid, a milky lotion, a paste, a cream, a gel, a solid, or a sheet.

The composition may be any of those which can be used for cosmetics, quasi-drugs, and drugs and can be used as skin care cosmetics such as lotions, milky lotions, creams, beauty essences, dispersions, gels, ointments, facial masks, spray types, mousses, aerosols, poultices, and cleansing agents.

The method for makeup of the present invention comprises: (A) applying to the skin the composition X; and (B) applying to the skin the composition Y. The order of application of the composition X and composition Y is not limited, and it is sufficient that either of the steps comprises applying to the skin the composition X. For example, the composition Y may be applied after the composition X is applied, the composition X may be applied after the composition Y is applied, or further, the composition X and/or composition Y may be applied a plurality of times before or/and after either of the steps.

The application method is not particularly limited, and the composition may be either applied or, in the case of a liquid, sprayed or the like, to the skin.

The composition X and composition Y used in the present invention can be used to provide a cosmetic kit for use in applying to a skin, comprising these composition X and composition Y.

Regarding the above-described embodiments, the present invention further discloses the following methods and the like.

<1> A method for makeup comprising:

(A) applying to a skin a composition X comprising components (A1) and (A2):

(A1) a polymer comprising a norbornane moiety and/or a silicone-modified Pullulan; and (A2) a volatile oil; and (B) applying to the skin a composition Y comprising a component (B1), other than the composition X:

(B1) one or more selected from the group consisting of polyols and liquid oils.

<2> The method for makeup according to the above <1>, wherein the component (A1) is preferably (A11) a polymer comprising a norbornane moiety, more preferably a silicone-modified polymer containing a norbornane moiety, even more preferably a polymer having a repeating unit of the following formula (1) or (2):

(1)

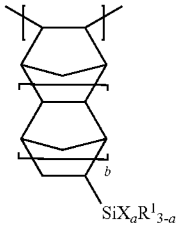

wherein $R^1$ is each independently an alkyl group having one or more and 12 or less carbon atoms, and X is a group of the following formula (i). a is an integer of 1 or above and 3 or below, and b is an integer of 0 or above and 2 or below.

(i)

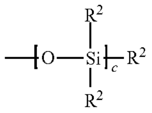

wherein $R^2$ is each independently a hydrocarbon group having one or more and 12 or less carbon atoms, and c is an integer of 1 or above and 5 or below.

(2)

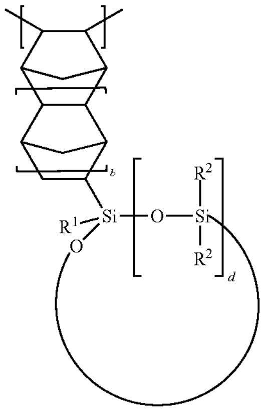

wherein $R^1$, $R^2$, and b are the same as described above, and d is an integer of 2 or above and 5 or below.

<3> The method for makeup according to the above <1> or <2>, wherein the component (A1) is preferably a silicone-modified polynorbornene of the following formula (6), more preferably a (norbornene/tris(trimethylsiloxy)silylnorbornene)copolymer.

(6)

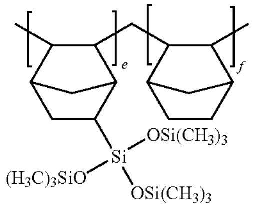

wherein e and f are the numbers of repeating units and each independently an integer of 1 or above.

<4> The method for makeup according to the above <3>, wherein, in the component (A), in the formula (6), a ratio of e and f, e/f, is preferably from 20/80 to 90/10 (mol/mol), more preferably from 30/70 to 80/20 (mol/mol), even more preferably from 50/50 to 70/30 (mol/mol).

<5> The method for makeup according to the above <1>, wherein the component (A1) is preferably (A12) a silicone-modified *Pullulan*, more preferably a *Pullulan* having a silicone structure in a side chain, even more preferably a silicone-modified *Pullulan* in which at least some hydrogen atoms of an OH group in the *Pullulan* is substituted with a group of the following formula (7), even more preferably tri(trimethylsiloxy)silyl propyl carbamic acid *Pullulan*.

$$—Z^1—SiX_aR^1_{3-a} \quad (7)$$

wherein $Z^1$ is a single bond or divalent organic group. $R^1$, X, and a are the same as described above, and in the same view, X is preferably trimethylsiloxy group, and a is preferably 3.

<6> The method for makeup according to any one of the above <1> to <5>, wherein a content of a solid content of the component (A1) is preferably 0.01 mass % or more, more preferably 1 mass % or more, even more preferably 2 mass % or more, even more preferably 4 mass % or more, even more preferably 5 mass % or more, and preferably 30 mass % or less, more preferably 28 mass % or less, even more preferably 25 mass % or less, even more preferably 20 mass % or less, and even more preferably 18 mass % or less in the composition X.

<7> The method for makeup according to any one of the above <1> to <6>, wherein the component (A2) is preferably one or more selected from the group consisting of volatile silicone oils and volatile hydrocarbon oils, more preferably one or more selected from the group consisting of isododecane, hexamethyldisiloxane, methyl trimethicone, and polydimethylsiloxane having kinematic viscosity of 2 cSt or lower at 25° C., even more preferably one or more selected from the group consisting of isododecane, hexamethyldisiloxane, methyl trimethicone, and octamethylpolydimethylsiloxane <8> The method for makeup according to any one of the above <1> to <6>, wherein the component (A2) is preferably one or more selected from the group consisting of volatile silicone oils and volatile hydrocarbon oils, more preferably one or more selected from the group consisting of isododecane, hexamethyldisiloxane, and polydimethylsiloxane having kinematic viscosity of 1.5 cSt or lower at 25° C., even more preferably one or more selected from the group consisting of hexamethyldisiloxane and polydimethylsiloxane having kinematic viscosity of 1 cSt or lower at 25° C., even more preferably hexamethyldisiloxane.

<9> The method for makeup according to any one of the above <1> to <8>, wherein the content of the component (A2) is preferably 1 mass % or more, more preferably 30 mass % or more, even more preferably 50 mass % or more, even more preferably 70 mass % or more, and preferably 98 mass % or less, more preferably 97 mass % or less, even more preferably 94 mass % or less, even more preferably 93 mass % or less in the composition X.

<10> The method for makeup according to any one of the above <1> to <9>, wherein a mass ratio of the component (A1) to the component (A2), (A1)/(A2), is preferably 0.002 or higher, more preferably 0.02 or higher, even more preferably 0.04 or higher, even more preferably 0.05 or higher, and preferably 1 or lower, more preferably 0.7 or lower, even more preferably 0.4 or lower, even more preferably 0.2 or lower in the composition X.

<11> A method for makeup comprising:
(A) applying to the skin a composition X comprising components (A1) and (A2):
(A1) from 0.01 to 30 mass % of a silicone-modified polymer containing a norbornane moiety; and
(A2) from 1 to 98 mass % of one or more volatile oil selected from the group consisting of volatile silicone oils and volatile hydrocarbon oils; and
(B) applying to the skin a composition Y comprising a component (B1), other than the composition X:
(B1) from 1 to 95 mass % of one or more selected from the group consisting of polyols and liquid oils.
<12> The method for makeup according to any one of the above <1> to <11>, wherein the component (B1) is (B11) a polyol, preferably one or more selected from the group consisting of dihydric alcohols and trihydric alcohols, more preferably comprises one or more selected from the group consisting of polyethylene glycol, dipropylene glycol, butylene glycol, propanediol, and glycerin, even more preferably comprises at least glycerin.
<13> The method for makeup according to any one of the above <1> to <11>, wherein the component (B1) is (B12) a liquid oil, preferably one or more selected from the group consisting of straight or branched hydrocarbon oils, ester oils, higher alcohols having a straight or branched alkyl or alkenyl group having from 10 to 24 carbon atoms, silicone oils, and phenoxyethanol, preferably one or more selected from the group consisting of straight or branched hydrocarbon oils, ester oils, silicone oils, and phenoxyethanol, more preferably one or more selected from the group consisting of liquid paraffin, squalane, hydrogenated polyisobutene, neopentyl glycol dicaprate, glyceryl monostearate monomyristate, polydimetylsiloxane, and phenoxyethanol.
<14> The method for makeup according to any one of the above <1> to <13>, wherein the content of the component (B1) is preferably 1 mass % or more, more preferably 5 mass % or more, even more preferably 10 mass % or more, and preferably 95 mass % or less, more preferably 80 mass % or less, even more preferably 40 mass % or less in the composition Y.
<15> The method for makeup according to any one of the above <1> to <14>, wherein the composition X further comprises preferably (A3) a powder, more preferably an inorganic powder.
<16> The method for makeup according to the above <15>, wherein the content of the component (A3) is preferably 0.1 mass % or more, more preferably 1 mass % or more, even more preferably 2 mass % or more, even more preferably 3 mass % or more, and preferably 40 mass % or less, more preferably 20 mass % or less, even more preferably 15 mass % or less, even more preferably 10 mass % or less in the composition X.
<17> The method for makeup according to any one of the above <1> to <16>, wherein the composition X can further comprise (A4) a surfactant, preferably a nonionic surfactant, more preferably a nonionic surfactant having HLB of from 1 to 7. <18> The method for makeup according to the above <17>, wherein the content of the nonionic surfactant is preferably 30 mass % or less, more preferably 10 mass % or less, even more preferably 5 mass % or less, even more preferably 3 mass % or less, even more preferably 1 mass % or less in the composition X.
<19> The method for makeup according to any one of the above <1> to <18>, wherein in the composition X, the content of water is preferably 50 mass % or less, more preferably 30 mass % or less, even more preferably 10 mass % or less, even more preferably 5 mass % or less, even more preferably 1 mass % or less in the composition X.
<20> The method for makeup according to any one of the above <1> to <19>, wherein the composition Y is applied after the composition X is applied.
<21> The method for makeup according to any one of the above <1> to <19>, wherein the composition X is applied after the composition Y is applied.
<22> A cosmetic kit for use in applying to a skin, comprising:
(A) a composition X comprising components (A1) and (A2):
(A1) a polymer comprising a norbornane moiety and/or a silicone-modified *Pullulan*; and
(A2) a volatile oil; and
(B) a composition Y comprising a component (B1), other than the composition X:
(B1) one or more selected from the group consisting of polyols and liquid oils.
<23> A cosmetic kit for use in applying to a, comprising:
(A) a composition X comprising components (A1) and (A2):
(A1) from 0.01 to 30 mass % of a silicone-modified polymer containing a norbornane moiety; and
(A2) from 1 to 98 mass % of one or more volatile oils selected from the group consisting of volatile silicone oils and volatile hydrocarbon oils; and
(B) a composition Y comprising a component (B1), other than the composition X:
(B1) from 1 to 95 mass % of one or more selected from the group consisting of polyols and liquid oils.

EXAMPLES

The present invention is described below with reference to examples, but the scope of the present invention is not limited to these examples. Of note, various measurements and assessments were performed by the following methods in the examples.

(Absence of Uncomfortable Feeling (Creakiness) Immediately after Application)

Five expert panelists applied each composition to the skin, and then, sensory evaluation was performed with the following criteria to assess an uncomfortable feeling of the skin. The result was expressed as the sum of scores given by the five panelists.

5; No uncomfortable feeling (creakiness) of the skin is felt at all.
4; No uncomfortable feeling of the skin is felt.
3; An uncomfortable feeling of the skin is not much felt.
2; An uncomfortable feeling of the skin is slightly felt.
1; An uncomfortable feeling of the skin is felt.

(Adhesiveness of Film)

Five expert panelists applied each composition to the skin, and then, sensory evaluation was performed with the following criteria to assess adhesiveness between the coating film and the skin. The result was expressed as the sum of scores given by the five panelists.

5; The skin and the coating film are attached to each other, and no twists occur.
4; The skin and the coating film are attached to each other, and not much twists occur.
3; The skin and the coating film are attached to each other, and twists slightly occur.
2; The coating film floats from the skin, and twists occur.
1; The coating film floats from the skin, and twists markedly occur.

(Appearance of Film (Transparent))

Five expert panelists applied each composition to the skin, and then, sensory evaluation was performed with the following criteria to assess transparency of the coating film. The result was expressed as the sum of scores given by the five panelists.

5; Highly transparent.
4; Transparent.
3; Slightly transparent.
2; Not much transparent.
1; Not transparent.

(Appearance of Film (Natural))

Five expert panelists applied each composition to the skin, and then, sensory evaluation was performed with the following criteria to assess natural finish of the coating film. The result was expressed as the sum of scores given by the five panelists.

5; Looks considerably natural.
4; Looks natural.
3; Looks slightly natural.
2; Does not look much natural.
1; Does not look natural.

Examples 1 to 8, Comparative Examples 1 to 3

Compositions X having the compositions shown in Table 1 and compositions Y having the compositions shown in Table 2 were manufactured, and the compositions each were applied to the skin by the steps shown in Table 3.

At this time, absence of an uncomfortable feeling (creakiness) immediately after application, adhesiveness of the film, appearance of the film (transparent), and appearance of the film (natural) were assessed. The result are shown in Table 3.

(Manufacturing Method)

(1) Composition X:

An oil phase component obtained by mixing the components (A1) and (A2) and other components were dispersed with a disperser and stirred with a homo mixer to obtain each of the compositions X.

(2) Composition Y:

The components (B11) and (B12) and other components were dispersed by stirring, and then stirred with a homo mixer to obtain each of the compositions Y.

(Application Method)

In Examples 1 to 5, Examples 7 and 8, and Comparative Example 2, an appropriate amount of the composition Y of each of the examples was applied with a palm to the area from the lips to the entire cheek in a half of the face of a subject, and then, an appropriate amount of the composition X was applied with fingers thereto.

In Example 6 and Comparative Example 3, an appropriate amount of the composition X of each of the examples was applied with fingers to the area from the lips to the entire cheek in a half of the face of a subject, and then, an appropriate amount of the composition Y was applied with a palm thereto.

In Comparative Example 1, an appropriate amount of the composition X was applied with fingers to the area from the lips to the entire cheek in a half of the face of a subject.

TABLE 1

| | Component (mass %) | Raw material name | Composition X | | | | | |
|---|---|---|---|---|---|---|---|---|
| | | | 1 | 2 | 3 | 4 | 5 | 6 |
| Component (A1) | (Norbornene/ tris(trimethylsiloxy)silylnorbornene copolymer solid content*1 | NBN-30-ID manufactured by Shin-Etsu Chemical Co., Ltd. | 13.0 | 13.0 | 2.0 | 18.0 | | |
| | Silicone-modified Pullulan solid content*2 | TSPL-30-ID manufactured by Shin-Etsu Chemical Co., Ltd. | | | | | 13.0 | |
| Others | Acrylic silicone solid content*3 | KP-550 manufactured by Shin-Etsu Chemical Co., Ltd. | | | | | | 13.0 |
| Component (A2) | Hexamethyldisiloxane | KF-96L-0.65cs manufactured by Shin-Etsu Chemical Co., Ltd. | 56.7 | 51.5 | 77.1 | 34.8 | 51.5 | 51.5 |
| | Isododecane | Marukasol R manufactured by Maruzen Petrochemical Co., Ltd. | 30.3 | 30.3 | 15.7 | 42.0 | 30.3 | 30.3 |
| Component (A3) | Dimethicone-treated silica | SA-SB-300 (refractive index: 1.54; average particle size: 3-7 μm) manufactured by Miyoshi Kasei, Inc. | | 5.0 | 5.0 | 5.0 | 5.0 | 5.0 |
| Others | Polyglyceryl diisostearate-2 | COSMOL 42V manufactured by The Nisshin OilliO Group, Ltd. | | 0.2 | 0.2 | 0.2 | 0.2 | 0.2 |
| | Total | | 100.0 | 100.0 | 100.0 | 100.0 | 100.0 | 100.0 |
| | (A1) | | 13.0 | 13.0 | 2.0 | 18.0 | 13.0 | 0.0 |
| | (A2) | | 87.0 | 81.8 | 92.8 | 76.8 | 81.8 | 81.8 |
| | (A3) | | 0.0 | 5.0 | 5.0 | 5.0 | 5.0 | 5.0 |

*1 to *3 in Table 1 are as follows:

*1: "NBN-30-ID" (an isododecane solution of a norbornene/tris(trimethylsiloxy)silylnorbornene copolymer with e/f of 60/40 (mol/mol) in the following formula (6) and Mn of 360,000; effective concentration: 30 mass %) manufactured by Shin-Etsu Chemical Co., Ltd.

(6)

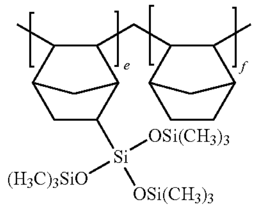

*2: "TSPL-30-ID" (an isododecane solution of tri(trimethylsiloxy)silyl propyl carbamide acid Pullulan; effective concentration: 30 mass %) manufactured by Shin-Etsu Chemical Co., Ltd. was dried under reduced pressure at 50° C. for 12 hours, and the obtained solid content was used.

*3: "KP-550" (an isododecane solution of a graft copolymer containing an acrylic polymer and polydimethylsiloxane, effective concentration: 40 mass %) manufactured by Shin-Etsu Chemical Co., Ltd. was dried under reduced pressure at 50° C. for 12 hours, and the obtained solid content was used.

TABLE 2

| (Skin lotion Y) | | | (Skin milky lotion Y) | | |
|---|---|---|---|---|---|
| | (Component) | (mass %) | | (Component) | (mass %) |
| | Purified water | 74.308 | | Purified water | 74 |
| (B11) | Glycerin | 10 | (B12) | Methylpolysiloxane | 5 |
| (B11) | Dipropylene glycol | 4 | | Ethyl p-hydroxybenzoate | 0.1 |
| (B11) | 1,3-Propanediol | 4 | | Methyl p-hydroxybenzoate | 0.4 |
| (B11) | Polyethylene glycol | 4 | (B11) | 1,3-Butylene glycol | 0.5 |
| (B11) | Polyoxyethylene glucoside | 1 | (B11) | Glycerin | 10 |
| | L-arginine | 0.001 | | Petrolatum | 0.5 |
| | 2-(2-hydroxyethoxy)ethylguanidine succinate | 0.5 | | Carboxyvinyl polymer | 0.2 |
| | pH modifier | 0.15 | (B12) | Neopentyl glycol dicaprate | 3.5 |
| | Sodium hyaluronate (aqueous ethanol solution) | 0.1 | | Stearyl alcohol | 0.4 |
| (B11) | Highly polymerized polyethylene glycol | 0.001 | | Cetanol | 0.6 |
| | Hydroxypropyl guar gum | 0.025 | | Sodium N-stearoyl-N-methyltaurate | 0.5 |
| | Xanthan gum | 0.03 | | Polyoxyethylene lauryl ether sodium phosphate | 0.3 |
| | Polyoxyethylene octyldodecyl ether | 0.2 | | Sorbitan monostearate | 0.2 |
| (B12) | Silicone oil | 0.05 | | Polyoxyethylene sorbitan monostearate | 0.2 |
| (B12) | Glyceryl monostearate monomyristate | 0.1 | | Ceramide | 1 |
| (B12) | Neopentyl glycol dicaprate | 0.1 | | Plant extract | 1.5 |
| (B12) | Squalane | 0.03 | | pH modifier | 0.1 |
| (B12) | Phenoxyethanol | 0.4 | | Perfume | 1 |
| | Plant extract | 1 | | Total | 100 |
| | Perfume | 0.005 | | | |
| | Total | 100 | | | |

TABLE 3

| | | Example 1 | Example 2 | Example 3 | Example 4 | Example 5 | Example 6 |
|---|---|---|---|---|---|---|---|
| | Step 1 | Skin lotion Y | Skin lotion Y | Skin lotion Y | Skin lotion Y | Skin milky lotion Y | Composition X-2 |
| | Step 2 | Composition X-1 | Composition X-2 | Composition X-3 | Composition X-4 | Composition X-2 | Skin milky lotion Y |
| | Step 3 | — | — | — | — | — | — |
| Evaluation | Absence of uncomfortable feeling immediately after application | 23 | 23 | 25 | 20 | 25 | 25 |
| | Favorable adhesiveness to the skin | 25 | 22 | 24 | 25 | 21 | 22 |
| | Appearance of film (transparent) | 25 | 24 | 22 | 24 | 22 | 22 |
| | Appearance of film (natural) | 21 | 25 | 25 | 21 | 21 | 20 |

| | | Example 7 | Example 8 | Comparative Example 1 | Comparative Example 2 | Comparative Example 3 |
|---|---|---|---|---|---|---|
| | Step 1 | Skin lotion Y | Skin lotion Y | Composition X-2 | Skin lotion Y | Composition X-6 |
| | Step 2 | Skin milky lotion Y | Skin milky lotion Y | — | Composition X-6 | Skin milky lotion Y |
| | Step 3 | Composition X-2 | Composition X-5 | — | — | — |
| Evaluation | Absence of uncomfortable feeling immediately after application | 25 | 18 | 10 | 7 | 8 |
| | Favorable adhesiveness to the skin | 20 | 17 | 9 | 7 | 8 |
| | Appearance of film (transparent) | 21 | 16 | 9 | 9 | 9 |
| | Appearance of film (natural) | 24 | 17 | 9 | 9 | 9 |

The invention claimed is:

1. A method for makeup comprising:

(A) applying to a skin a composition X comprising components (A1) and (A2) at a mass ratio of the component (A1) to the component (A2), (A1)/(A2), of from 0.02 to 18/76.8:

wherein (A1) comprises a norbornene/tris(trimethylsiloxy)silylnorbornene) copolymer and a content of the component (A1) in the composition X is from 2 to 30 mass %; and (A2) comprises one or more volatile oils selected from the group consisting of isodecane and hexamethyldisiloxane; and (B) applying to the skin a composition Y comprising a component (B1), other than the composition X:

wherein (B1) comprises one or more selected from the group consisting of polyols and liquid oils, wherein said composition Y is applied before or after applying said composition X.

2. The method for makeup according to claim 1, wherein a content of the component (A2) in the composition X is from 1 to 98 mass %.

3. The method for makeup according to claim 1, wherein a content of the component (B1) in the composition Y is from 1 to 95 mass %.

4. A cosmetic kit for use in applying to a skin, comprising:

(A) a composition X comprising components (A1) and (A2) at a mass ratio of the component (A1) to the component (A2), (A1)/(A2), of from 0.02 to 18/76.8:

wherein (A1) comprises a norbornene/tris(trimethylsiloxy)silylnorbornene) copolymer and a content of the component (A1) in the composition X is from 2 to 30 mass %; and (A2) comprises one or more volatile oils selected from the group consisting of isodecane and hexamethyldisiloxane; and (B) a composition Y comprising a component (B1), other than the composition X:

wherein (B1) comprises one or more selected from the group consisting of polyols and liquid oils.

5. The kit according to claim 4, wherein a content of the component (A2) in the composition X is from 1 to 98 mass %.

6. The kit according to claim 4, wherein a content of the component (B1) in the composition Y is from 1 to 95 mass %.

* * * * *